United States Patent [19]
Barborak et al.

[11] Patent Number: 5,362,962
[45] Date of Patent: Nov. 8, 1994

[54] METHOD AND APPARATUS FOR MEASURING PIPELINE CORROSION

[75] Inventors: Darren M. Barborak, Pickerington; William A. Bruce, Columbus, both of Ohio

[73] Assignee: Edison Welding Institute, Columbus, Ohio

[21] Appl. No.: 48,788

[22] Filed: Apr. 16, 1993

[51] Int. Cl.$^5$ .............................................. H01J 3/14
[52] U.S. Cl. .................................... 250/234; 250/571
[58] Field of Search ............... 250/562, 563, 571, 572, 250/234; 356/376, 237

[56] References Cited

U.S. PATENT DOCUMENTS

| | | | |
|---|---|---|---|
| 3,612,693 | 10/1971 | Stevenson | 356/376 |
| 4,201,475 | 5/1980 | Bodlaj | 356/381 |
| 4,212,534 | 7/1980 | Bodlaj | 356/1 |
| 4,708,482 | 11/1987 | Neiheisel | 356/376 |
| 4,786,815 | 11/1988 | Walker et al. | 250/560 |
| 4,798,469 | 1/1989 | Burke | 356/376 |
| 4,800,104 | 1/1989 | Cruickshank | 427/230 |
| 4,908,508 | 3/1990 | Dubbledam | 250/225 |
| 4,937,445 | 6/1990 | Leong et al. | 250/237 |
| 4,952,226 | 8/1990 | Frazee, Jr. et al. | 65/3.12 |
| 4,978,223 | 12/1990 | Kutchenriter et al. | 356/384 |

OTHER PUBLICATIONS

Nippon Kokan Technical Report, "Inspection Pig Systems for Offshore Pipeline", Overseas No. 39 (1983), pp. 113–119.

Nippon Steel Technical Report, "Development of System for Inspecting Buried Gas Pipelines for External Corrosion Thickness Loss", No. 44, Jan. 1990, pp. 43–49.

MVS Modular Vision Systems Inc., product literature, "LaserVision Sensor MVS-10 Specifications", 1US patent #4,859,829, Aug. 22, 1989.

*Primary Examiner*—David C. Nelms
*Attorney, Agent, or Firm*—Watkins, Dunbar & Pollick

[57] ABSTRACT

An automatic corrosion measurement system and method enables rapid measurement and evaluation of corrosion on significant portions of straight and curved pipe sections and other surfaces from several square inches to several square feet, using a laser instrument which projects laser light across a scan area which includes corrosion, and detects reflected laser light therefrom. A positioning mechanism advances the laser instrument along the surface to permit evaluation of a large area, and a processor controls both the operation of the laser instrument and positioning mechanism. Automatic processing by the processor converts surface condition signals into readily usable output in the form of displays, printouts or maps, for immediate use.

33 Claims, 6 Drawing Sheets

METHOD AND APPARATUS FOR MEASURING PIPELINE CORROSION

BACKGROUND OF THE INVENTION

The present invention relates to the measurement of pipeline corrosion, and in particular, to a laser mapping apparatus and method for evaluating external and internal pipeline corrosion.

Pipeline maintenance requires early and accurate detection of external corrosion in buried steel pipe. External corrosion detection is, initially, typically conducted from within the pipeline using in-line inspection vehicles (e.g. smart pigs) or from outside the pipeline using equipment to detect the leakage of cathodic protection current. Smart pigs typically utilize either magnetic flux leakage, eddy current or ultrasonic technology, or a combination thereof. After removal of scale by water blasting and other techniques, external corrosion is typically further evaluated by visual inspection.

Once an area of corrosion has been detected, corrosion measurement and evaluation follow. Typically, the pipeline is excavated and grit blasted in the area of corrosion in preparation for more accurate measurement of corrosion and pitting. There are several methods for manually measuring pitting, some using simple instruments such as pit gauges, scale and straight edge, wire contour gauges, and bridging bars with micrometers, and others using complex equipment such as ultrasonic detectors and radiographic equipment, all of which have their disadvantages.

Internal corrosion is evaluated using similar techniques, with cleaning, inspection and measurement techniques limited by the accessibility and purpose of the pipe, and type of material carried by the pipe.

Regardless of which surface of the pipeline is evaluated, once the effected area has been measured and depth of pits therein determined, the remaining wall thickness and strength of the corroded pipe is evaluated using one of several available algorithms. Informed decisions can then made whether to repair or replace the corroded section of pipe or allow it to remain in service.

Although generally effective, known methods and equipment for measuring pitting have several drawbacks. For example, known methods are performed primarily in a longitudinal direction along straight pipe sections, obviating desirable evaluation of elbows, bends and curved circumferential portions of pipe surfaces. In addition, existing corrosion measurement instruments have mechanical limitations which further restrict measurement of corrosion to small areas or points. As a result, evaluation of a larger area requires continual movement of instruments in two dimensions to establish a grid of data, and such movement introduces errors in the data. Thus, known methods typically obtain data whose accuracy and resolution is low. Where pipe diameters prevent entry, access to internal surfaces is limited to surfaces near openings.

Complex corrosion measurement instruments have further drawbacks. In particular, ultrasonic detectors, although accurate for point measurement, require transducer access to the bottom of the pit or fluid coupling of the transducer and pipe, making it very messy for evaluation of excavated pipes. Radiographic equipment presents an x-ray hazard to operators, and films produced require further time and equipment for development and analysis. Moreover, while radiography is good for qualitative detection of corrosion, it is not an accurate technique for quantitative measurement of corrosion. As a result, known methods for corrosion measurement are not only mechanically limited, but are also expensive and time consuming because of the labor involved to perform the method, process data, and interpret the results.

Accordingly, the need exists for a cost-effective automatic corrosion analysis apparatus and method which enables rapid measurement and evaluation of significant portions of both straight and curved corroded pipe sections.

SUMMARY OF THE INVENTION

The present invention satisfies that need by providing an automatic corrosion measurement system and method which enables rapid measurement and evaluation of corrosion on significant portions of straight and curved pipe sections, from several square inches to several square feet, with related cost savings. Cost savings further result from improved accuracy, as decisions on removal or repair of pipe sections can be made with greater certainty, eliminating unnecessary repairs required when using conservative approaches necessary with less accurate techniques. Further, more reliable repairs can be made, which require lower factors of safety, providing further cost savings.

The automatic corrosion measurement system of the present invention includes a laser instrument which emits laser light to, and detects reflected laser light from, an area of a surface which includes corrosion. A positioning mechanism is connected to the laser instrument for positioning, and a processor is connected to control the operation of the laser instrument and positioning mechanism and receive and process signals therefrom.

Preferably the laser instrument includes a laser source, such as a laser diode or gas laser, which produces a laser light; means for projecting the laser light across an area of the surface generally defining a scan area thereacross generally oriented in a direction of scanning; and a laser light detector to receive laser light reflected from the surface. Projecting the laser beam across the surface to define a scan area oriented in a direction of scanning makes it possible for the positioning mechanism to move the laser instrument in just one other direction of movement to evaluate an area, thus reducing positioning errors, and enhancing precision, accuracy and speed.

The means for projecting the laser light establishes a field of view for the laser instrument which is typically wedge shaped or trapezoidal, and produces a narrow generally rectangular or substantially linear scan area upon the surface. The means for projecting may comprise a means for repeatedly scanning a laser beam across the scan area. Preferably, the means for projecting includes means for spraying the laser beam in a constant pattern to constantly define the scan area, such as by diffraction or refraction of a laser beam by an element. Alternatively, the means for projecting is simply a means for defining a field of laser light projected from a source, such as a baffle shape to define the radially projecting output from a laser diode and produce a field of view for the laser instrument.

In accordance with the present invention, the laser light reflected from the scan area back to the laser light detector produces surface condition signals. Meanwhile, the positioning mechanism produces related position signals identifying the location of the scan area. Both the surface condition and position signals are received by the processor means. Preferably, the processor means automatically processes those signals to produce data related to corrosion on the scan area, and thereby eliminates time consuming and labor intensive processing and analysis. As the positioning mechanism moves the laser instrument along the surface, data is obtained from a series of adjacent scan areas along the path of the laser instrument, thus permitting the system to evaluate the overall area of interest defined on the surface.

The present invention is capable of automatic operation to evaluate corrosion on both flat and curved surfaces. For example, the positioning mechanism may be mounted on or in a pipe for travel in a generally circumferential or longitudinal direction to evaluate areas previously beyond the capability of existing corrosion evaluation apparatuses and methods.

In a further aspect of the present invention, a method for measuring corrosion on a surface is provided which can be used to measure curved surfaces, such as pipe elbows, pipe circumferences, and flat surfaces. The method includes the initial steps of defining an area for surface corrosion analysis, providing an automatic corrosion measuring system as previously described, and locating the positioning mechanism and laser instrument thereof relative to the defined area of interest. The method next calls for measuring corrosion by projecting laser light across a portion (the scan area) of the defined area of interest, and generating surface condition signals thereby; advancing the laser instrument with the positioning mechanism in a direction of movement along the defined area and generating position signals therewith; and receiving the related surface condition signals and position signals at the processor means.

Preferably the scan area is a generally rectangular and substantially linear area which encompasses both non-corroded portions of the surface (which provide a frame of reference) and corroded portions where pitting or general corrosion may be detected by the system of the present invention. The steps of projecting, advancing and receiving are repeatedly performed either stepwise or simultaneously as the laser instrument is positioned along a path in the direction of movement to measure the entire defined area of interest. Finally, automatic processing of the data is performed to provide readily usable output related to surface corrosion in the defined area of interest. The output may be used to identify pitting, and to evaluate the amount of remaining material and its strength.

Accordingly, it is an object of the present invention to provide an apparatus and method which may be applied to measure corroded surfaces of various types, curved or flat. It is another object of the present invention to provide an apparatus and method which may be applied to measure corrosion on internal and/or external surfaces of a pipeline. It is a further object of the present invention to provide a system and method for measuring corrosion with greater precision, accuracy and speed than existing methods. It is a further object of the present invention to provide a system and method for corrosion measurement which is easy to use, portable, and adaptable for field use. It is a further object of the present invention to provide an automatic system and method for corrosion measurement which obtains, processes and produces data related to surface corrosion which is easily understood. It is a still further object of the present invention to reduce the time and cost of corrosion analysis. These and other objects, features and advantages of the present invention will be apparent from the drawings, detailed description and claims which follow.

Figure 1:
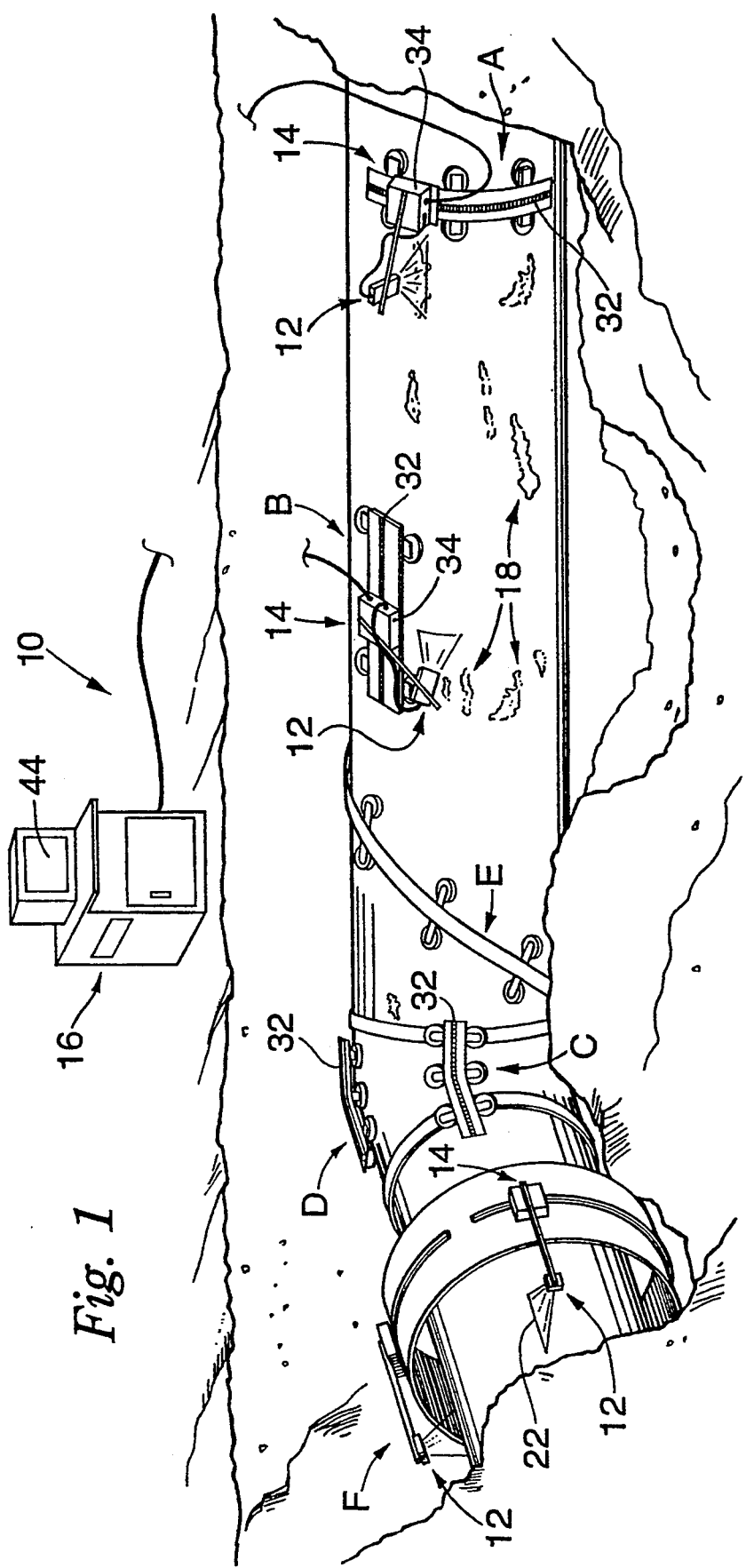
FIG. 1 is a schematic perspective view of the present invention variously configured to measure corrosion on straight and curved surfaces in a representative application.

In the following description of the preferred embodiments of the invention, which are illustrated in the drawings, specific terminology is used for the sake of clarity. However, it is not intended that the invention be limited to the specific terms selected or the system so shown and it is to be understood that each specific term includes all technical equivalents which operate in a similar manner to accomplish a similar purpose.

DETAILED DESCRIPTION OF THE PREFERRED EMBODIMENT

Referring to FIG. 1, the automatic corrosion measurement system 10 of the present invention is shown having a laser instrument 12, a positioning mechanism 14 connected to said laser instrument, and a processor means 16 connected to control the laser instrument and positioning mechanism. As shown, the system 10 is capable of measurement and evaluation of corrosion 18 on significant portions of both straight and curved pipe sections as well as other surfaces, from several square inches to several square feet, depending primarily on the optics. The automatic corrosion measurement system 10 may also be referred to herein as an automatic surface mapping apparatus.

Figure 2:
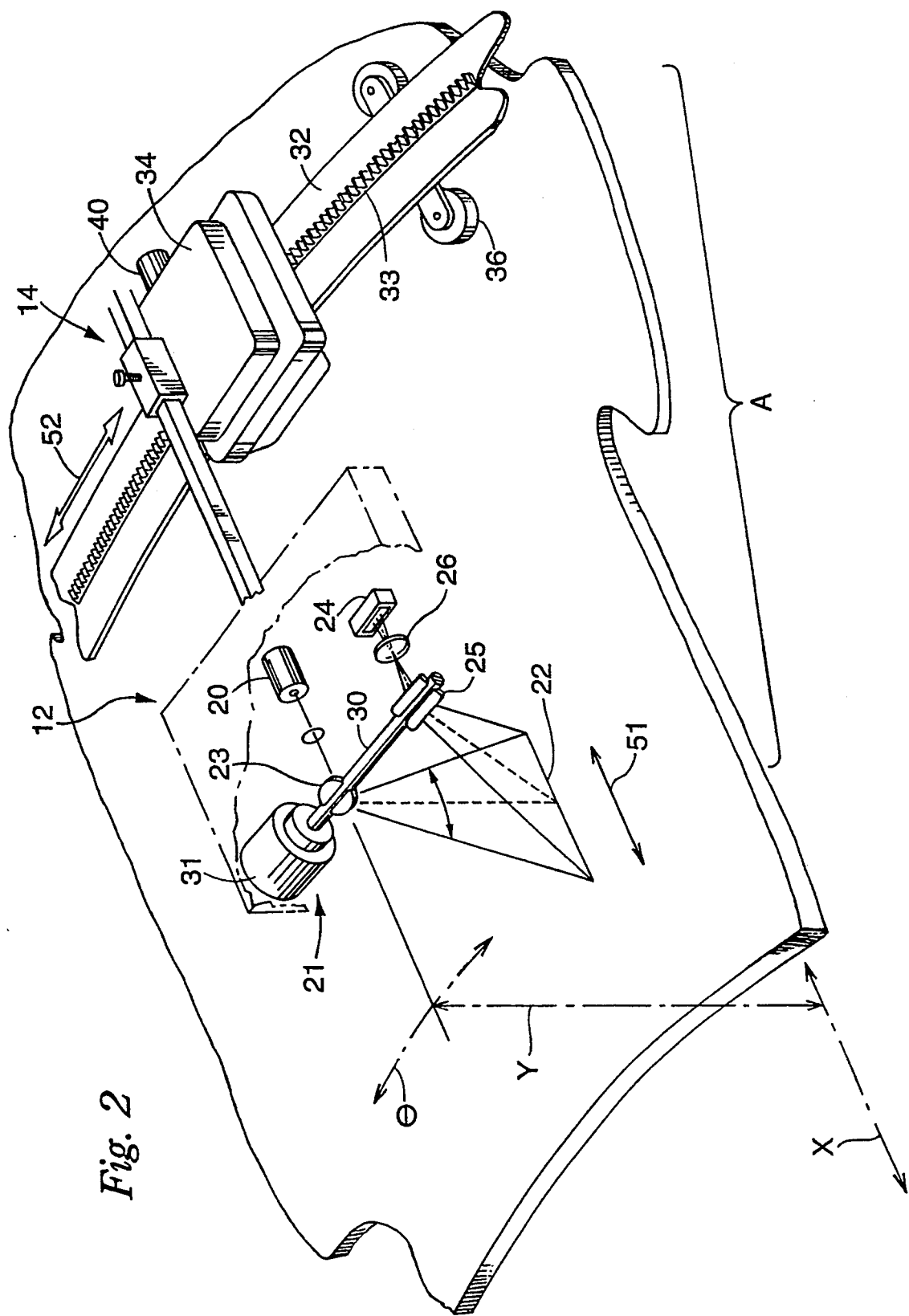
FIG. 2 is a detailed schematic perspective view of the laser instrument of the present invention in one configuration of FIG. 1.

As shown in further detail in FIG. 2, the laser instrument 12 includes a laser source 20, means 21 for projecting laser light across a surface and a laser light detector 24. In the laser instrument 12, the laser source 20 is conventional, such as a laser diode or gas laser, for example a 5 mW helium-neon laser. All known lasers, including those producing visible, infrared and ultraviolet light, may be used. The means 21 for projecting the laser light establishes a field of view for the laser instrument which is typically either wedge-shaped or trapezoidal, and produces a narrow, generally rectangular or substantially linear scan area 22 on the surface. Laser light reflected from the surface to be measured is detected by the laser light detector 24.

The means 21 for projecting may comprise a means for scanning repeatedly a laser beam across the scan area 22. In that case, a beam constantly moves from one end of the scan area 22 to the other to trace the scan area 22. Preferably the means 21 for projecting includes means for spraying the laser beam in a constant pattern to constantly define the scan area 22, such as by diffraction or refraction of a laser beam by an element. Alternatively, the means 21 for projecting is simply a means for defining a field of laser light projected from a source 20, such as a baffle shaped to define the radially projecting output from a laser diode and produce a field of view for the laser instrument.

Means for scanning repeatedly a laser beam typically receive a laser light beam from a laser source 20, and cause the laser light beam to trace across a portion (i.e. the scan area 22) of the surface. As shown in FIG. 2, the means for scanning preferably includes a dithering or rotating multi-faced mirror 23 mounted on a rod 30 which alternately rotates through an arc by action of a motor 31 to trace the beam across the scan area 22. Further, preferably, a second reflecting mirror 25 is mounted on rod 30 to move in coordination with the mirror 23 to cause laser light reflected from the scan area 22 to remain aligned on the light detector 24 during the scan. A collecting lens 26 may further be used to refocus the reflected light. Where means for scanning are used, the portion of the area scanned by each sweep of the laser beam is dependent upon the optics of the mirror 23, second reflecting mirror 25, and collecting lens 26, where such is used. As well, the means for scanning may produce scan lines by other means, such as movement of the laser source 20 itself. The present invention is not intended to be limited by the means employed in the preferred and alternative embodiments.

Laser instruments are commercially available which include a laser source 20, detector 24, and means for scanning, and which may be adapted for use in accordance with the present invention. Such laser instruments include the Seampilot ® optical profile sensor system available from Oldelft Corporation of America, Fairfax, Va. or Delft instruments, Delft, Netherlands.

Means for spraying the laser beam constantly spray laser light simultaneously across the entire scan area 22. Preferably such a spray is created by receiving a laser light beam in a refracting element, which refracts the laser light beam to form a wide beam. Such means are commercially available. Means for defining a field of laser light preferably limit the projection of laser light from a point source such as a laser diode, and may be any number of baffle arrangements which produce a constant field of laser light along the entire scan area 22. Laser instruments are commercially available which include a laser source 20 and detector 24 as well as necessary means to produce a spray or field of laser light, and may be adapted for use in accordance with the present invention. Such laser instruments include the MVS-10, MVS-20 and MVS-30 LaserVision Sensors made by MVS Modular Vision Systems, Inc., Montreal, Quebec, Canada; and the Saturn ™ and Jupiter ™ Range Finders made by Servo-Robot, Boucherville, Quebec, Canada.

Detector 24 is preferably a charge-coupled device (CCD camera), which detects and records the pattern and intensity of laser light reflected from the scan area 22. Other suitable detectors 24 which accomplish the same result are understood to be within the scope of this element of the invention. Such detectors 24 may be, by way of example not limitation, CCD arrays, photodiode arrays, TDI arrays, and photodetectors, such as Si, Ge, Pbs, and InGaAs photodetectors. As well, other suitable means 21 for projecting which accomplish the same result are understood to be within the scope of this element of the invention.

Regardless of the method and means 22 for projecting laser light, the number of scans per second may be varied by the user, and multiple scans of the same area may be taken. Typically, reciprocating or repeatably scanning laser instruments are capable of a maximum of ten scans per second, with approximately 200 points per scan, while spraying laser instruments are typically capable of up to 60 scans per second, with approximately 480 points per scan. The charge coupled device light detectors 24 are capable of sampling the reflected light along with its angular position every 400 microseconds to produce a measured point which is sent to the processor means 16. In this way approximately 200 or more measured points may be so obtained per scan when the laser source 20 produces 10 scans per minute.

A surface profile of the scanned area may be derived from the reflected light by the processor means 16 in accordance with the known principles applicable to charge coupled devices, using triangulation and the known geometry and path of the laser light traveling between the laser source 20 and the detector 24.

Still referring to FIGS. 1 and 2, the positioning mechanism 14 of the present invention preferably includes a track 32, curved, straight, spiral or helical, rigid, flexible, or articulated, and disposed on or relative to a surface to be measured, and a controllable means for driving the laser instrument 12 on the track 32, such as a tractor 34 having one or more drive motors. The drive motors are preferably electric, but may also be hydraulic or other known drives. The operation of the tractor 34 is preferably automatically controlled by processor means 16, but may also be accomplished in increments by an operator.

In accordance with the exemplary application to the outside surface of a pipe in of FIGS. 1 and 2, for purposes of analysis, the tractor 34 may be considered to lie either within a two axis or three axis polar coordinate system (X, Y, Θ), with the longitudinal direction the X-axis, the height above the pipe surface along the Y-axis, and the circumferential location the Θ-axis (see FIG. 2). As further shown in FIG. 1, the track 32 can be mounted in numerous configurations, with the laser instrument 12 always fixed in the Y-axis at a height relative to the surface of the pipe. In a first configuration, indicated at A, the laser instrument 12 and tractor 34 travel in the Θ-axis direction while scanning in a direction generally parallel to the x-axis. In a second configuration, indicated at B, the laser instrument 12 and tractor 34 travel in the X-axis direction while scanning in a direction generally along the Θ-axis direction. Other configurations are possible, as indicated at C, D, E and F, and bends or elbows can be also be measured using the first configuration A. It is understood that such polar coordinates may be used for like motion where the corrosion measurement system of the present invention measures corrosion on the inner surface of a pipe.

Preferably, the track 32 is removably connected to the surface to be measured by magnetic means 36, such as fixed or activated magnets. However, other removable connecting means, such as straps 38 (representatively shown in FIG. 1), clamps, brackets, studs, frames, vacuum gripping, or the like, may be used as required by the application to secure the positioning mechanism 14 relative to the surface.

As well, the positioning mechanism 14 may include a movable or fixed carriage 54, positioned by spacers 55 (e.g. bearing surfaces, wheels, etc) relative to a surface or pipe surface to be measured, which carries the track 32 or multiple tracks 32 as indicated at F in FIG. 1. As such, the track 32 is not attached to the surface to be measured, but is spaced therefrom.

The tractor 34 is mechanically connected to the track 32. The track 32 shown in FIGS. 1 and 2 preferably includes an area or groove including teeth 33 which can intermesh with a drive gear (not shown) connected to or driven by the drive motor of tractor 34. Anti-backlash gearing is preferably incorporated in the tractor drive motor to control the position of the laser instrument 12 in any position on the track 32. Track 32 and tractors 34 which may be adapted for use in accordance with the present invention are commercially available, for exampled tracks and KAT ® P-Type, programmable travel carriage available from Gullco International Inc., Cleveland, Ohio. Movable carriages which clamp around, and travel along pipes are available from CRC-Evans, Houston, Tex. It is understood that the term movable carriages 54 also includes frames and structures, such as pipeline pigs and similar vehicles, which travel along the inside surfaces of pipelines.

Figure 3:
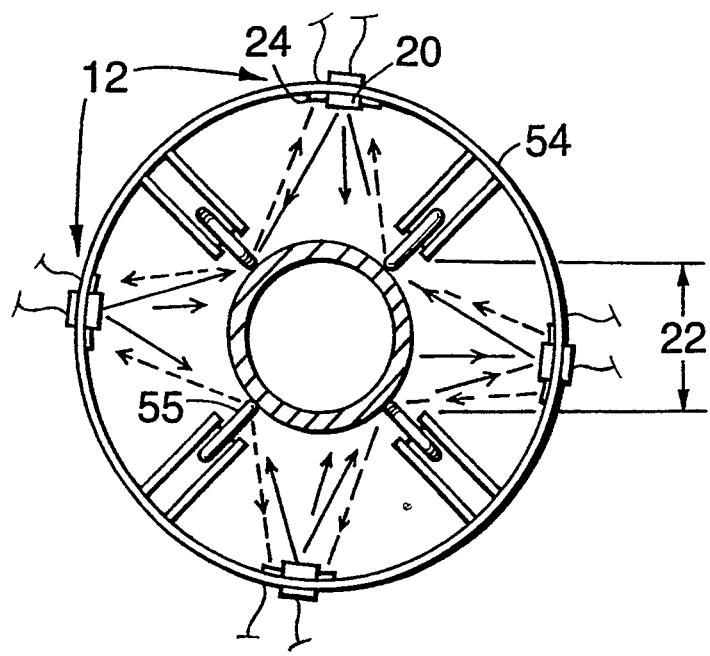
FIG. 3 is a schematic cross-sectional view of the present invention in one configuration using a movable carriage.

Multiple laser instruments 12 may be used simultaneously in accordance with the present invention, and may be positioned by a single tractor 34, or by separate, dedicated tractors 34, to increase the speed and capacity with which a surface area of interest is evaluated. For example, as shown in FIG. 2, multiple laser instruments 12 may be mounted on a movable carriage 54, such as made by CRC-Evans. Carriage 54 may be used to support tracks 32 or an attached structure including tracks 32 which carry the laser instruments 12, each dedicated to move and evaluate a series of scan areas 22 over an assigned arc of a pipe. Again, some original, substantially non-corroded portion of the pipe surface is desired as a reference. Where multiple laser instruments 12 are used, known carriage geometry and overlap between scan areas 22 can be used to accurately interrelate the surface condition and position data. Alternatively, as shown in FIG. 3, multiple laser instruments 12 may be fixed in position and include means for spraying laser light to continuously measure scan areas 22 over an assigned arc or area for corrosion measurement of all or part of an annular surface area of a pipe. Regardless whether fixed or movable laser instruments 12 are used, the means 21 for projecting projects laser light from ones of the laser light sources 20 across respective scan areas 22 which are related in a predetermined pattern, facilitating evaluation of large areas with minimal motion of laser instrument 12.

Further, where corrosion measurements are made with multiple laser instruments 12 over portions of an annular inner or outer surface area of a pipe using a traveling carriage 54, random displacement of the carriage 54 occurring relative to the surface of the pipe can be corrected by the processor means 16 by reference to such corrosion measurements. Movable carriages 54 may be advanced along a pipe by various means 58 for advancing known in the art which may include, by way of example and not limitation, connection to a train of pipeline cleaning or analysis equipment, powered cables, gas pressure, or separate carriage drive mechanisms. The precise means used is not critical to the present invention, whether the movable carriage 54 is outside or inside a pipe.

Still further shown in FIG. 2 is a distance tracking device 40 which precisely measures the position of the laser instrument 12 along the track 32, in either the X-axis or Θ-axis direction. Preferably the distance tracking device 40 comprises an optical encoder, such as the incremental encoders and absolute rotary encoders available from Parker-Hannifin Corp., Rohnart Park, Calif. Such devices may be driven by an axle of the drive motor of the tractor 34 or attached to another such driven element of the positioning mechanism 14 for distance measurement. Other types of optical encoders or precision distance measuring devices which generate an electronic signal may be suitable for this purpose.

Figure 4:
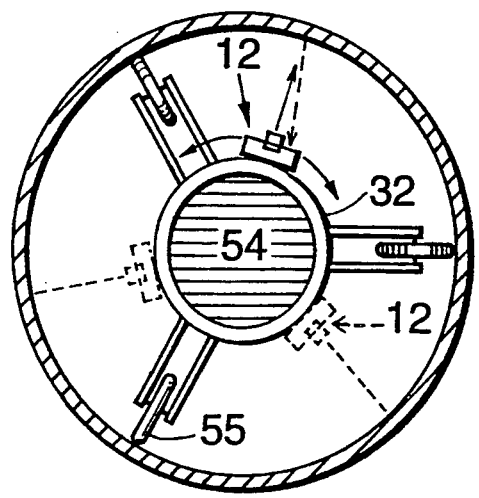
FIG. 4 is a schematic cross-sectional view of a representative configuration using a movable laser instrument to evaluate corrosion on the inner surfaces of a pipe.
Figure 5:
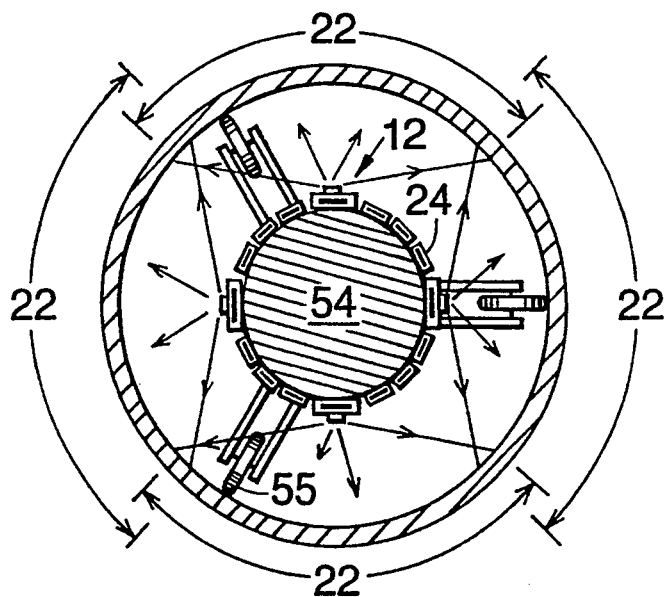
FIG. 5 is a schematic cross-sectional view of a representative configuration using fixed position laser instruments in combination to evaluate corrosion on the inner surfaces of a pipe.
Figure 6:
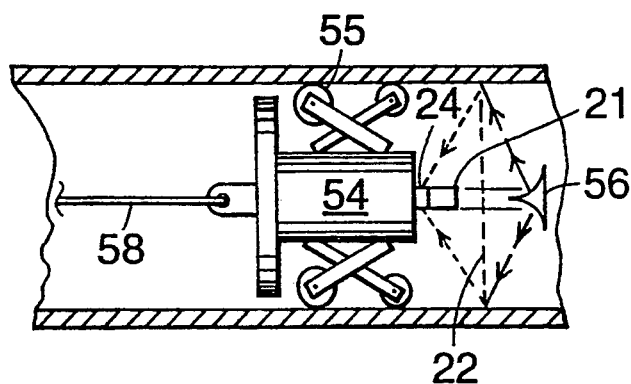
FIG. 6 is a schematic cross-sectional view of a representative configuration using a single fixed position laser instrument to evaluate corrosion on the inner surfaces of a pipe.

Single or multiple laser instruments 12, on any of the positioning mechanisms 14 discussed, using any of the various means 21 for projecting, may be used for evaluating inside surfaces, such as the inside surfaces of a pipeline. Illustrative uses of carriage mounted laser instruments 12 in a pipeline are shown in FIGS. 4–6. It is understood that track sections 32 may also be separately placed or mounted on inside surfaces to be measured without using carriages 54.

In FIG. 4, a single track-mounted laser instrument 12 is mounted on track 32 to evaluate an annular area of the pipe surface. Scan area 22 extends perpendicular to the page. Multiple laser instruments 12 may also be used in concert, as indicated in phantom. FIG. 5 shows the use of fixed position laser instruments 12 using means for spraying laser light to measure corrosion in assigned scan areas 22. In smaller diameter pipes, it may be necessary to mount the laser instruments such that the laser source 20 and/or light detector 24 are diametrically disposed as far as possible from the surface to be measured. FIG. 6 shows the use of a single laser instrument 12 having a single laser source 20, and including optical means 56 for distributing a constant beam of laser light across a scan area 22. The scan area 22 is illustratively shown to include a circumferential or annular area on the inner surface of a pipeline.

Accordingly, in operation, projecting the laser beam across the surface to define a scan area 22 oriented in a direction of scanning makes it possible for the positioning mechanism 14 to move the laser instrument 12 in just one other direction of movement to evaluate a defined area, thus reducing positioning errors, and enhancing precision, accuracy and speed. Operation of the laser instrument 12 produces surface condition signals, while movement of the positioning mechanism 14 generates surface condition signals. Positioning mechanism 14 can move laser instrument 12 either stepwise between scans, or simultaneously during scans to measure the entire defined area of interest. Thus, for example, where means for scanning are used, the scan areas 22 may be in generally parallel relationship, or where means for scanning repeatedly are used, may be a zigzag pattern of connected scan areas 22. Where measurement is made while the positioning mechanism 14 moves the laser instrument 12, a series or spiral or helical scan areas 22 may be obtained. Regardless, the positioning mechanism 14 moves the laser instrument 12 in a direction of motion (i.e. second direction) indicated generally at 52 which is, preferably, although not necessarily, generally transverse relative to the direction of scanning (i.e. first direction) indicated generally at 51 to generate position signals at the distance tracking device 40. Both types of signals are received by the processor means 16, as is preferred.

The scan area 22 is preferably sideboard to the track 32. Although not preferred, increased scanning range may be obtained by mounting the laser instrument 12 on a second tractor and short lateral track (not shown) disposed on the tractor 34 to permit shifting the laser instrument 12 laterally (i.e. generally transverse to the second direction 52). A second distance tracking device (not shown) can be used in like manner as distance tracking device 40 to identify the lateral location of the laser instrument 12. As such, measurement of surface corrosion can be achieved by positioning or "indexing" the laser instrument 12 so that no unnecessary motion is required. For example, the positioning mechanism 14 may first position the laser instrument 12 along the $\Theta$-axis direction in a first direction, reposition the laser instrument 12 in the x-axis direction using the second tractor, and then return along the $\Theta$-axis direction in the opposite direction. Thus, surface measurement is made on both passes. Other shifting means may be used to controllably shift the laser instrument 12 a known distance, and achieve the same desired effect. Alternatively, where a carriage 54 is used, the carriage may be used to shift the laser instrument 12 along the x-axis direction after each pass to allow parallel scan areas 22 to be evaluated incrementally.

The processor means 16 of the present invention is best shown in FIG. 1. The processor means 16 may be centralized in a portable unit 42, or portions of the processor means 16 linked but separately located with and/or dedicated to the laser instrument 12, tractor 34, and/or other components. The processor means 16 may, thus, for example be made of one or more microprocessors. Regardless of the configuration, at least some portion of the processor means 16 is located apart from the laser instrument 12 and positioning mechanism 14 and, preferably, cable connected to the positioning mechanism 14 and/or laser instrument 12, as representatively shown in FIG. 1, to control and receive data therefrom. Alternatively., these components may be wirelessly interconnected. Data received by the processor means 16 may be processed to provide graphical, visual or tabular information or output regarding the surface scanned, and may be further processed to determine the remaining wall thickness and the remaining strength of the scanned material, such as a pipe. Further processing may be incorporated to provide recommendations concerning repair of surfaces which have been scanned. A keyboard 43 and a data output device 44, e.g. a printer, plotter, display (shown), and the like, or combination thereof, is preferably provided to permit operator interface with the processor means 16.

In operation of the present invention the laser instrument 12 produces surface condition signals and the positioning mechanism 14 produces related position signals, both of which are received by the processor means 16. Processing of data from overlapping scan areas 22 may be undertaken automatically, based upon the known, fixed relation between the scan areas 22 based on the position signals. Preferably, the production of surface condition and position signals is automatic, and the processor means 16 automatically processes those signals to produce data related to corrosion on the area of the surface measured. Programming for automatic operation of both the laser instrument 12 and positioning mechanism 14, as well as automatic signal processing, are within the capability of one skilled in the art. The data may be processed in real time, or downloaded into memory for later processing.

Figure 7:
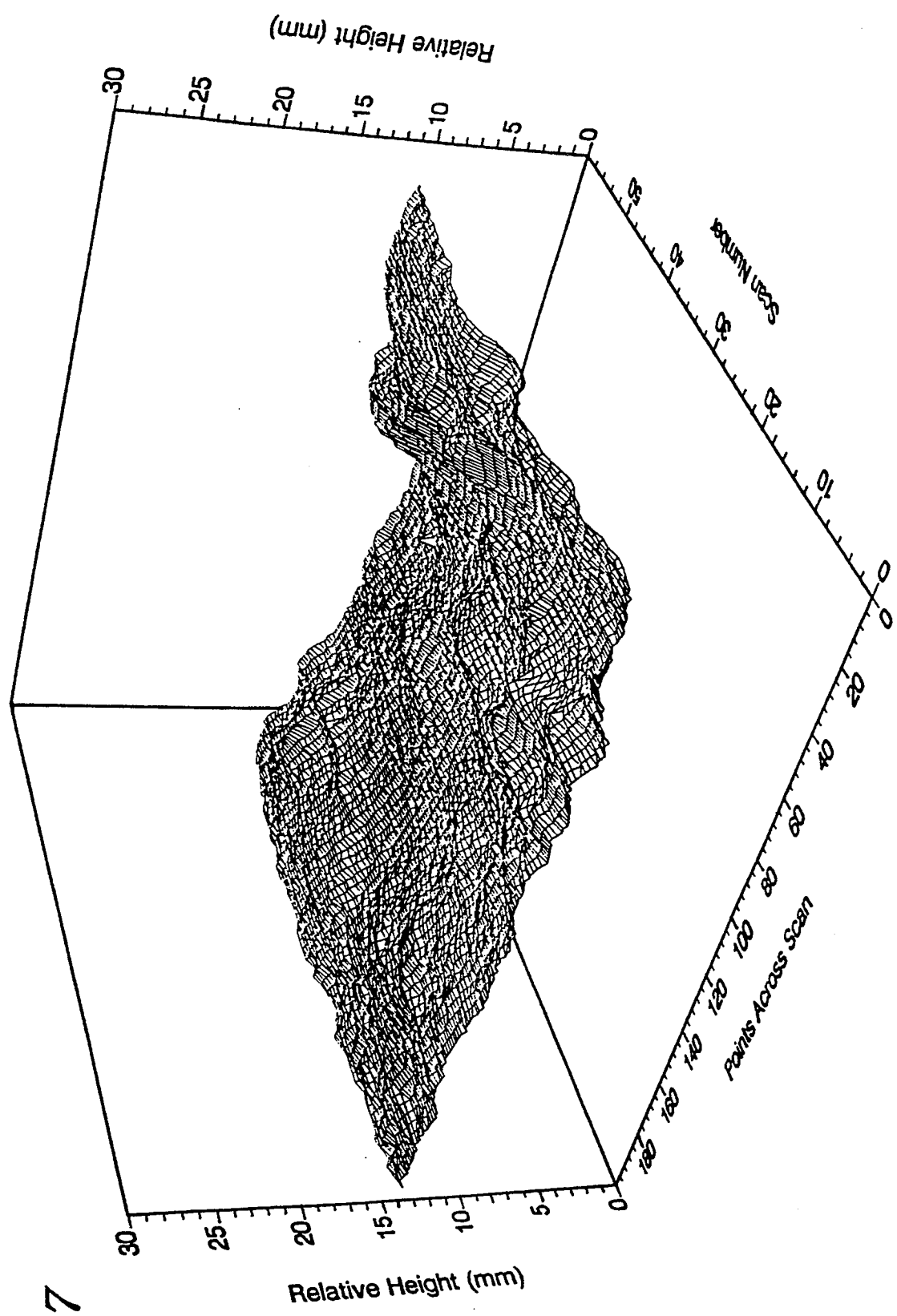
FIG. 7 is a representative plot of surface corrosion developed from surface condition and position data for a corroded specimen.

As previously described, in operation of the present invention the positioning mechanism 14 moves the laser instrument 12 along the surface to obtain data from a series of scans to permit evaluation of the overall area desired. An example of data produced by approximately 60 scans, converted into cartesian coordinates, and plotted in three dimensions, is shown in FIG. 7. Typically, the approximately 200 measured points are processed by the processor means 16 to a sequence of straight line-segments by means of a piecewise approximation algorithm. For example a scan of 201 points would be reduced to a maximum of 33 data points. The scope and quality of data which is available from the combination of the laser source 20, detector 24 and distance tracking device 40 permits the system 10 to obtain extremely accurate surface measurements. Detection of surface height variations of $\pm 0.15$ millimeters (mm) is possible, and the minimum distance between points across a scan is 0.25 mm. Accuracy from one scan to another is controlled primarily by the positioning mechanism 14. The more slowly the laser instrument 12 is moved along the path of travel, e.g. the second direction 52, the more accurate the data is from one scan to the next. Due to the number of scans per second, the positioning mechanism 14 moves the laser instrument 12 in what appears to be a continuous motion.

As generally indicated in FIG. 1 by the application to buried pipes, the system 10 of the present invention is preferably portable and readily usable in the field, and the data output device 44 is capable of readily providing data in usable form in the field. FIGS. 3 and 4 illustrate such readily usable data.

Figure 8:
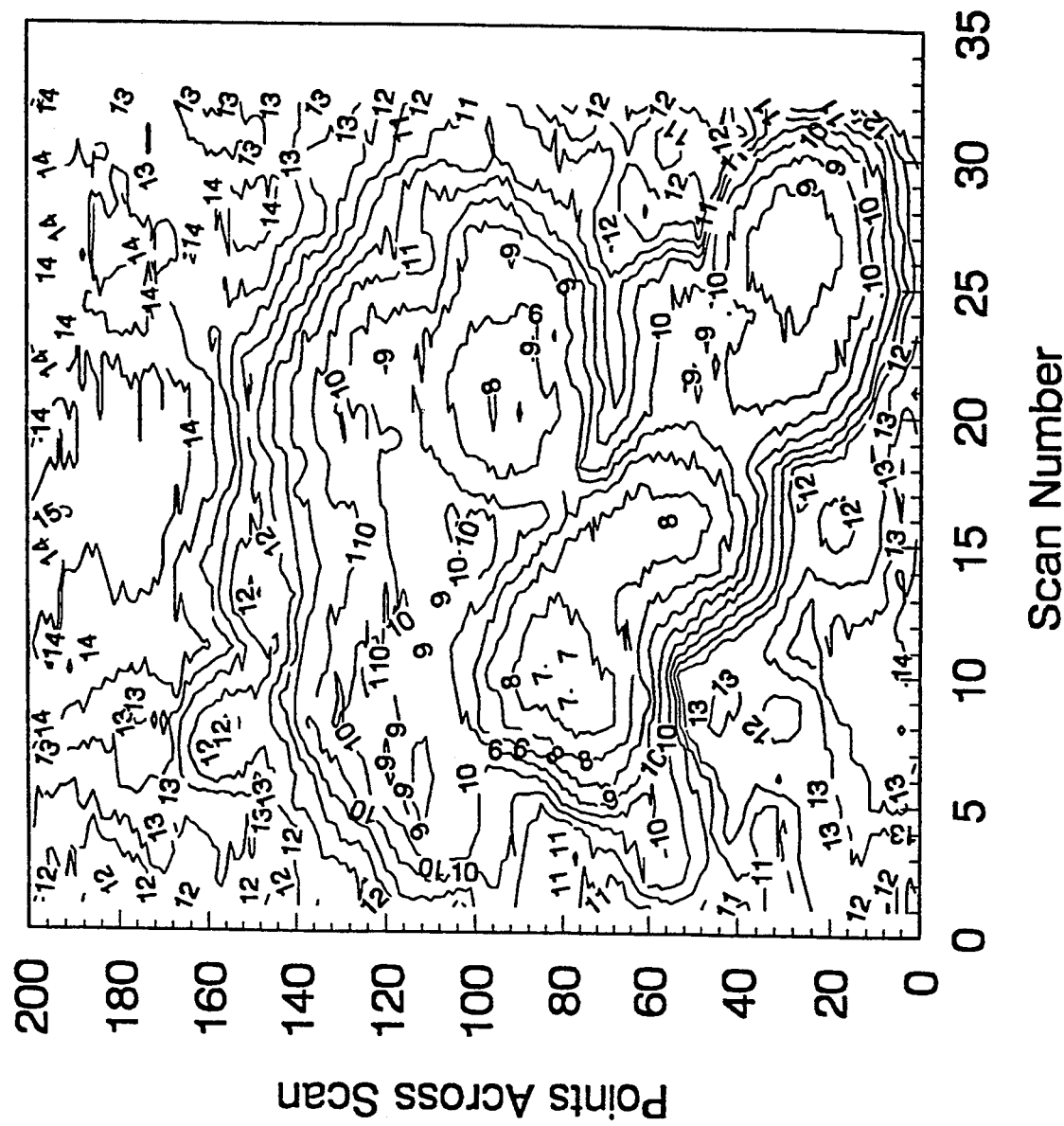
FIG. 8 is a representative plot of contours derived from FIG. 7 projected onto a plane surface for ease of analysis.

FIG. 8 shows a two-dimensional contour plot of FIG. 7 where the lines of equal height are connected, much like a topographic map. As may be seen, around the edges of the specimen areas of non-corrosion are indicated by numbers from 12 to 14, while areas of possible pitting are evident at the lines numbered 7 to 9. This was confirmed by visual analysis of the specimen, which located a pinhole at the bottom of the deepest pit. In addition, given the data obtained by the apparatus of the present invention, the effective area and depth of the pits may be determined. As well, remaining wall thickness and strength of the corroded pipe may be determined by using one of several available algorithms in the processor means 16. Two common algorithms are the generalized ANSI B31G computer analysis, commercially available from several sources, and the more advanced RSTRENG computer program, available from the American Gas Association, Arlington, Va. The RSTRENG program requires "river bottom analysis" of the data such as shown in FIG. 8, to identify the locus of lowest points (and thus greatest corrosion and pitting) as a precondition to its use.

In a further aspect of the present invention, a method for measuring corrosion on a surface is provided which may be applied to measure corrosion on either curved surfaces, such as the exemplary pipe elbows, pipe circumferences shown in FIG. 1, or flat surfaces. The method includes the initial steps of defining an area for surface corrosion analysis, providing an automatic corrosion measuring system 10, and locating the positioning mechanism 14 and laser instrument 12 thereof relative to the area of the surface to be measured. The automatic corrosion measuring system 10 is preferably as described above, including a laser instrument 12 having means for projecting laser light to define a scan area 22 within the defined area of interest which scan area 22 is generally oriented in a direction of scanning 51; a positioning mechanism 14 connected to the laser instrument 12; and processor means 16 to control the laser instrument 12 and the positioning mechanism 14. The details of the system 10 are considered incorporated herein by reference without further restatement thereof for discussion of the method of the present invention.

Where applied to analysis of buried pipelines, the step of defining an area for surface corrosion analysis may further include the initial steps of locating, excavating, and cleaning the pipe. Cleaning may occur by grit blasting which removes substantially loosened scale but does not erode the wall thickness of the pipe. In defining the area for analysis, any of the conventional corrosion detection methods may be used to identify an area of interest for further evaluation, including but not limited to the use of in-line inspection methods (e.g. smart pigs), detection of leakage of cathodic protection current, and visual inspection coincident with take-up and relay (recoating) processes. Where corrosion on inner surfaces of a pipeline is measured, the step of cleaning may include different methods, such as wire brushing and, where necessary, drying the pipeline surface.

The method next calls for measuring corrosion in the scan area 22 with the laser instrument 12 and generating surface condition signals thereby; advancing the laser instrument 12 with the positioning mechanism 14 in a direction of movement (or second direction) 52 along the defined area and generating position signals therewith; and receiving the surface condition signals and position signals at the processor means 16. The scan area 22, preferably a narrow, generally rectangular or substantially linear area, preferably encompasses both corroded and non-corroded portions of the surface, so that the non-corroded portions provide a frame of reference for pitting detected in the corroded portions. Typically most buried pipes are smooth with discrete areas of visible corrosion, and the area of corrosion can be precisely evaluated and effectively mapped relative to the non-corroded portions. The steps of measuring, advancing and receiving are repeatedly performed, either stepwise or simultaneously, as the laser instrument 12 is positioned along a path in the second direction to measure or map the entire area of interest. Finally, automatic processing of the data is performed by the processor means 16 to provide readily usable output related to surface corrosion which may be used to identify pitting, and to evaluate the amount of remaining material and its strength. Further detailed steps may be understood to be within the scope of the method, as will be apparent from the description of the system and method above and the drawings.

In addition, the present method may be used in cooperation with other existing methods and equipment, as may be desired. For example, spot checking of pipe wall thickness with ultrasonic equipment may be desirable to confirm remaining wall thicknesses in pipes. While welded pipe has a substantially uniform wall thickness, seamless pipe may be produced with variations of wall thickness of ±15%, making such ultrasonic testing a useful additional test in some instances. A drawback of such testing is that the ultrasonic tests may not be used to accurately assess areas of corrosion which are smaller in diameter than the ultrasonic transducer itself (typically ½ inch in diameter).

The present invention permits measurement of corrosion to be automatically performed on straight, flat or curved surface areas, and on a straight or curved track 32. Precision, accuracy and speed are improved by the use of a means for projecting the laser light beam, and resulting need to position the laser instrument 12 in only one direction. The measurement of innumerable point sources in two dimensions relative to an independent frame of reference is thereby obviated. The method of the present invention may, further, be performed partially or completely automatically. Further, as illustrated by FIGS. 3 and 4, the step of automatically processing the surface condition signals and position signals, producing data related to corrosion on the surface, and displaying or printing that data as output in a usable form eliminates costly time consuming analysis.

All materials used in the system of the present invention are conventional unless otherwise indicated, and charge coupled devices, laser diodes, processors, data output devices, and motors described are commercially available components.

While certain representative embodiments and details have been shown for purposes of illustrating the present invention, it will be apparent to those skilled in the art that various changes in the system and method disclosed herein may be made without departing from the scope of the invention, which is defined in the appended claims.

What is claimed is:

1. An automatic corrosion measurement system comprising:
   a laser instrument emitting laser light to and detecting reflected laser light from an area of a surface to evaluate the condition thereof, said laser instrument including:
      a laser light source producing laser light;
      means for projecting laser light across an area of said surface to define a scan area; and
      a laser light detector positioned to detect laser light reflected from said scan a real and generating surface condition signals related to laser light reflected from said scan area; and
   a positioning mechanism removably mountable to a said surface and connected to said laser instrument, said positioning mechanism:
      defining a curvilinear direction of movement for said laser instrument along a portion of said surface; and
      generating position signals related to the position of said laser instrument along said curvilinear direction of movement; and
   processor means communicably connected to said laser instrument and said positioning mechanism for control thereof, wherein said processor means receives and processes said surface condition signals and position signals to produce data related to corrosion on said surface.

2. The system of claim 1 wherein:
   said laser source produces a laser light beam; and said means for projecting comprises means for repeatedly scanning a laser light beam across said scan area.

3. The system of claim 1 wherein:
said laser source produces a laser light beam; and
said means for projecting comprises means for spraying portions of said laser light beam in a constant beam across said scan area.

4. The system of claim 1 wherein said means for projecting comprises means for defining said laser light into an expanding field of laser light.

5. The system of claim 1 wherein said means for projecting produces a generally rectangular and substantially linear scan area oriented in a first direction, and said first direction is generally at an angle relative to said curvilinear direction of movement of said laser instrument.

6. The system of claim 1 wherein said laser instrument is mounted laterally relative to said positioning mechanism such that said scan area does not substantially cross the path of said positioning mechanism as it advances in said curvilinear direction of movement.

7. The system of claim 1 wherein said laser light detector is selected from the group consisting of: a charge coupled device, photodiode arrays, TDI arrays, and photodetectors.

8. The system of claim 1 wherein said positioning mechanism comprises a track removably connected in a fixed position to said surface.

9. The system of claim 8 wherein said positioning mechanism further comprises:
means for driving said laser instrument on said track; and
an automatic distance tracking device for automatically measuring the position of said laser instrument on said track and generating position signals related thereto.

10. The system of claim 9 wherein said distance tracking device comprises an optical encoder connected to said means for driving.

11. The system of claim 1 wherein said positioning mechanism comprises:
a carriage having spacer means separating said carriage from a surface to be measured; and
means for advancing said carriage along said surface.

12. The system of claim 11 wherein:
said system includes a plurality of laser instruments each having respective laser light sources producing laser light and respective means for projecting laser light; and
said plurality of laser instruments are positioned to project laser light across a plurality of scan areas, respectively, related in a pattern.

13. The system of claim 12 wherein said positioning mechanism further comprises:
a plurality of track sections; and
a plurality of means for driving said laser light sources on said track sections.

14. The system of claim 1 wherein at least a portion of said processor means is disposed on said positioning mechanism.

15. The system of claim 1 wherein said system is portable and is weather resistant for use in the field.

16. The system of claim 1 wherein said processor means comprises a data output device selected from the group consisting of an electronic display, a printer, a plotter, or a combination thereof.

17. The system of claim 1 wherein:
said processor means:
automatically controls the operation of said laser instrument;
automatically controls said positioning mechanism to position said laser instrument in said curvilinear direction of movement; and
automatically processes said surface condition and position signals to produce data related to corrosion on said surface.

18. The system of claim 1 wherein said positioning mechanism further includes means for shifting the position of said laser instrument laterally relative to said curvilinear direction of movement.

19. The system of claim 1 wherein said positioning mechanism defines both a curvilinear and a rectilinear direction of movement.

20. A method for measuring corrosion on a surface comprising the steps of:
defining an area for surface corrosion analysis;
providing an automatic corrosion measuring system including:
a laser instrument having:
a laser light source producing laser light;
means for projecting said laser light across an area of said surface to define a scan area; and
a laser light detector positioned to detect laser light reflected from said scan area and to generate surface condition signals related to laser light reflected from said scan area;
a positioning mechanism connected to said laser instrument, operable to position said laser instrument in a direction of movement along a portion of said surface, said positioning mechanism generating position signals related to the position of said laser instrument along said direction of movement; and
processor means communicably connected to said laser instrument and said positioning mechanism for control thereof, wherein said processor means receives and process said surface condition signals and position signals;
identifying a reference point on said surface within at least, one scan area, wherein said reference point is a substantially uncorroded portion of said surface;
locating said positioning mechanism and laser instrument relative to said reference point, independent of the location of said processor means, and generating a position signal therefor;
projecting laser light with said laser instrument across a scan area within said defined area for analysis with said laser instrument and generating surface condition signals with said laser instrument;
advancing said laser instrument with said positioning mechanism in a direction of movement along said area defined for analysis and generating position signals with said positioning mechanism as said laser instrument advances in said direction of movement;
receiving said surface condition signals and said position signals at said processor means; and
repeatedly performing said steps of projecting, advancing and receiving.

21. The method of claim 20 wherein said direction of movement is a curvilinear direction of movement, and said step of advancing comprises advancing said laser instrument in said curvilinear direction of movement.

22. The system of claim 21 wherein said step of advancing in a curvilinear direction of movement comprises advancing said laser instrument generally around the circumference of a pipe.

23. The system of claim 21 wherein said step of advancing in a curvilinear direction of movement comprises advancing said laser instrument generally along the bend of a pipe elbow.

24. The method of claim 20 wherein said steps of: projecting and generating surface condition signals with said laser instrument, advancing and generating position signals with said positioning mechanism, and receiving, are repeatedly performed automatically.

25. The method of claim 20 wherein said method further includes the step of automatically processing said surface condition signals and position signals to, and automatically producing data related to corrosion on said surface.

26. The method of claim 20 wherein:
said direction of movement is both a curvilinear and rectilinear direction of movement; and
said step of advancing comprises advancing said laser instrument in said curvilinear and rectilinear direction of movement.

27. The method of claim 21 wherein said step of providing an automatic corrosion measuring system includes providing a positioning mechanism a portion of which is removably mountable in a fixed position to a portion of said surface.

28. The method of claim 20 wherein said step of locating comprises locating said positioning mechanism in a curvilinear path, and defining said direction of movement as a curvilinear direction of movement.

29. A method for automatically measuring corrosion on an area of a surface comprising the steps of:
defining an area for surface corrosion analysis;
providing an automatic corrosion measuring system including a laser instrument projecting laser light along a scan area within said area defined for analysis, a positioning mechanism operable to position said laser instrument in a direction of movement along a portion of said surface, and processor means communicably connected to said laser instrument and said positioning mechanism for control thereof;
locating said positioning mechanism and said laser instrument, relative to said area defined for analysis, and generating a position signal therefor;
automatically measuring a plurality of at least partially overlapping scan areas along said portion of said surface with said laser instrument, and generating corresponding surface condition signals, including measuring within said portion at least one point of reference and at least one point of corrosion relative thereto;
automatically advancing said laser instrument with said positioning mechanism in said direction of movement in coordination with said step of automatically measuring, and generating corresponding position signals;
automatically receiving said surface condition signals and said position signals at said processor means; and
automatically processing said surface condition signals and position signals to produce data related to corrosion on said surface.

30. The method of claim 29 wherein:
said step of locating said positioning mechanism comprises locating said positioning mechanism in a curvilinear path; and
said step of automatically advancing advances said laser instrument along said curvilinear path.

31. The method of claim 29 wherein said steps of automatically measuring and automatically advancing are repeatedly performed in a stepwise manner to measure a plurality of scan areas in said area defined for analysis.

32. The method of claim 29 wherein said steps of automatically measuring and automatically advancing are repeatedly performed simultaneously to measure a plurality of scan areas in said area defined for analysis.

33. The method of claim 29 wherein said step of locating comprises locating said positioning mechanism in both a curvilinear and rectilinear path, thereby defining said direction of movement as both a curvilinear and rectilinear direction of movement.

* * * * *

UNITED STATES PATENT AND TRADEMARK OFFICE
CERTIFICATE OF CORRECTION

PATENT NO. : 5,362,962
DATED : November 8, 1994
INVENTOR(S) : Barborak et al.

It is certified that error appears in the above-identified patent and that said Letters Patent is hereby corrected as shown below:

Column 1, line 41, "can then made" should read -- can then be made --.
Column 6, line 49, "pipe in of FIGS." should read -- pipe in FIGS. --.
       line 61, "the x-axis" should read -- the X-axis --.
       line 66, "elbows can be also be" should read -- elbows can also be --.
Column 7, line 61, "ones of the laser light sources" should read -- one of the laser light sources --.
Column 9, line 27, "in the x-axis" should read -- in the X-axis --.
       line 34, "along the x-axis" should read -- along the X-axis --.
       line 50, "Alternatively., these" should read -- Alternatively, these --.
Column 12, lines 52-53, "mountable to a said surface" should read -- mountable to a portion of said surface --.

Signed and Sealed this

Twenty-first Day of February, 1995

Attest:

BRUCE LEHMAN

Attesting Officer        Commissioner of Patents and Trademarks